United States Patent [19]
Gaffar

[11] Patent Number: 6,045,097
[45] Date of Patent: Apr. 4, 2000

[54] DIALYSIS BAG HOLDER

[75] Inventor: Shaik A. Gaffar, 8800 Paso Robles Ave., Northridge, Calif. 91325

[73] Assignee: Shaik A. Gaffar, Northridge, Calif.

[21] Appl. No.: 09/036,622

[22] Filed: Mar. 7, 1998

[51] Int. Cl.[7] ........................................ B65B 1/04
[52] U.S. Cl. ............................ 248/95; 141/314; 141/391; 211/85.15; 248/146; 248/97
[58] Field of Search ...................... 248/146, 152, 248/95, 97; 211/71.01, 85.15, 72, 73; 141/314, 391

[56] References Cited

U.S. PATENT DOCUMENTS

| | | | |
|---|---|---|---|
| 1,827,731 | 10/1931 | Churchill | 211/72 X |
| 2,206,728 | 7/1940 | Nevins, Jr. | 211/73 |
| 3,964,709 | 6/1976 | LaBelle et al. | 211/73 X |
| 4,102,488 | 7/1978 | Morrow et al. | 248/97 X |
| 4,966,241 | 10/1990 | Luchinger et al. | 248/152 X |
| 5,366,192 | 11/1994 | Carroll | 248/152 |
| 5,386,958 | 2/1995 | Amato | 248/146 |

*Primary Examiner*—Derek J. Berger

[57] ABSTRACT

The invention described holds dialysis bag and other similar articles containing delicate membrane securely in place so that biological solution can be added or collected, safely. The Dialysis Bag Holder contains bottom, vertical and top plates, cradle tubes and a funnel holding mechanism. The bottom plate holds vertical plate and cradle tubes. The vertical plate, besides providing additional support to cradle tubes, holds the top plate firmly in place. The top plate located over the tip of cradle tubes, seats funnel for pouring large volume of sample. Cradle tubes, attached permanently at an angle to the top of bottom plate, hold dialysis bags. The angle of attachment makes cradle tubes have an ascending slope. The concave holding surface of cradle tube complements with the cylindrical body of the bag or similar articles. The entire unit provides stability to the dialysis bag before, during and after loading biological sample. The cradle tube not only provides open access to dialysis bag but also saves in its cup any sample spilled. The cup controls the lower part of dialysis bag closed with twine. The notch at the top of cup restrains the movement of bag closed with a clamp. The cradle tube is equally useful at the time of collection of dialyzed sample. Other embodiments incorporating modifications and substitutions also serve similar purposes. A major advantage of these Dialysis Bag Holders is that cradle tube permits loading of dialysis bags of varying lengths. By providing open access to bag, these units eliminate potential accidents leading to the loss of sample. All units are simple to use and easy to store.

14 Claims, 11 Drawing Sheets

DIALYSIS BAG HOLDER

CROSS-REFERENCE TO RELATED APPLICATIONS

Not applicable

STATEMENT REGARDING FEDERALLY FUNDED RESEARCH OR DEVELOPMENT

Not applicable

REFERENCE TO MICROFICHE APPENDIX

Not applicable

BACKGROUND OF THE INVENTION

This invention specifically relates to holding dialysis bag for adding and removing samples in biochemical and immunochemical studies.

In biochemical processes such as extraction, purification, conjugation and characterization excess reagents are removed from desired molecules by dialysis. To perform dialysis, a sample is taken in a bag with semipermeable membrane and stirred against buffer. With time, large molecules are retained inside the bag while small reagent molecules diffuse into buffer surrounding the bag. This selective retention of molecules is due to the presence of pores in the membrane of bag.

Prior to adding sample, one end of the dialysis tube is closed tightly either by putting a knot with twine or by using a clamp so that no liquid leaks. The first problem at this stage is holding the extremely thin and highly flexible bag erect so that liquid sample can be added. Ordinarily, a small portion at the top of bag is held in between a finger and thumb. Then, the bag is open and sample is added with a pipette. Most accidents happen at this point. Because attention is divided between holding the bag and adding sample, because one wears gloves and because membrane is extremely thin, hold on the dialysis bag becomes weak. A slip of the bag causes loss of valuable sample. If sample contains radioactive compounds, therapeutic drugs, toxins and other similar cytotoxic biologicals, surface contamination requires a cleanup.

The volume of sample for dialysis varies from time to time. For a sample of small volume, a pipette is used to add to dialysis bag. However, when sample volume is large, the second problem arises. Generally, this problem is addressed by using a funnel and a ring stand. The stem of funnel is inserted into the bag, held together tightly and then, sample is poured. Under the weight of added sample, the bag tends to slip from the hold. Therefore, the rest of the bag also needs support. Improper support makes the bag exert a downward pull causing, first slip and then spill of valuable sample. This method is cumbersome and the bag still needs support.

After adding sample, the bag is closed with twine or clamp. This step requires open access. The third problem arises at this step. Since the volume of sample and the height of bag vary, proper support and access is not always available. Commonly, the top of bag is held with fingers of one hand and the clamp is applied with the other hand. To close with twine, both hands are needed to tie a proper knot. This requires right kind of support with proper access to the bag. Alternately, help is needed from another person. Improper access for closing the bag, therefore, leads to potential risk of spilling the sample.

After closing, the bag is tested for leaks by gently squeezing, and then, dialyzed against suitable buffer. At the end of dialysis, sample is collected from the bag. The fourth problem arises at this stage. To collect dialyzed sample, first, the bag is held vertical and then, clamp is removed. If twine is used, the bag is cut slightly below the knot at the top. At this phase the bag definitely needs proper support to prevent from collapsing. Needless to say that support should also provide free and open access to the bag so that sample can be collected, properly. After collecting sample, empty bag is discarded.

In brief, giving proper support and holding securely in place are crucial not only for adding but also for collecting sample from the dialysis bag. Also, providing open access is essential for closing the bag before dialysis and for collecting the sample after dialysis. Providing a funnel where it is required greatly helps in adding large volume of sample to the dialysis bag.

The objects and advantages of this invention are:

(a) to fabricate a cradle from a tube so that dialysis bag can be held safely in place (b) to provide a bottom plate for holding cradle tube firmly (c) to attach cradle tube at an angle so that dialysis bag stays in place and also retains liquid sample without spilling (d) to provide quick and open access to dialysis bag (e) to furnish a cup at the bottom of cradle so that any sample spilled by accident can be saved (f) to provide additional support in the back of cradle tube (g) to provide a top plate with a hole for seating a funnel without needing a separate ring stand (h) to fabricate bottom, vertical and top plates from one piece of material without requiring the manufacturer use nuts and bolts (i) to provide transparency so that level of sample and the status of bag can be viewed clearly, and (j) to fabricate the unit from commonly available materials which are hard, durable and tough to break Further objects and advantages will be apparent from the following description and drawings.

BRIEF SUMMARY OF THE INVENTION

The invented Dialysis Bag Holder keeps dialysis sac securely in place for adding as well as for collecting biological solution, safely. The dialysis bag rests in a cradle tube that is attached permanently to a bottom plate at an angle. A vertical plate not only provides additional support to the cradle tube but also holds the top plate, firmly. The concave surface of cradle and the cylindrical body of the bag mutually complement and provide the best hold. Access to bag is open and immediate. For adding large volume of sample, top plate holds a funnel immediately above the bag. The bottom of cradle tube forms a cup to collect any accidentally spilled sample. The cup also restricts movement of the lower part of dialysis bag closed with twine or clamp. The unit is simple to use and easy to store.

Figure 1:
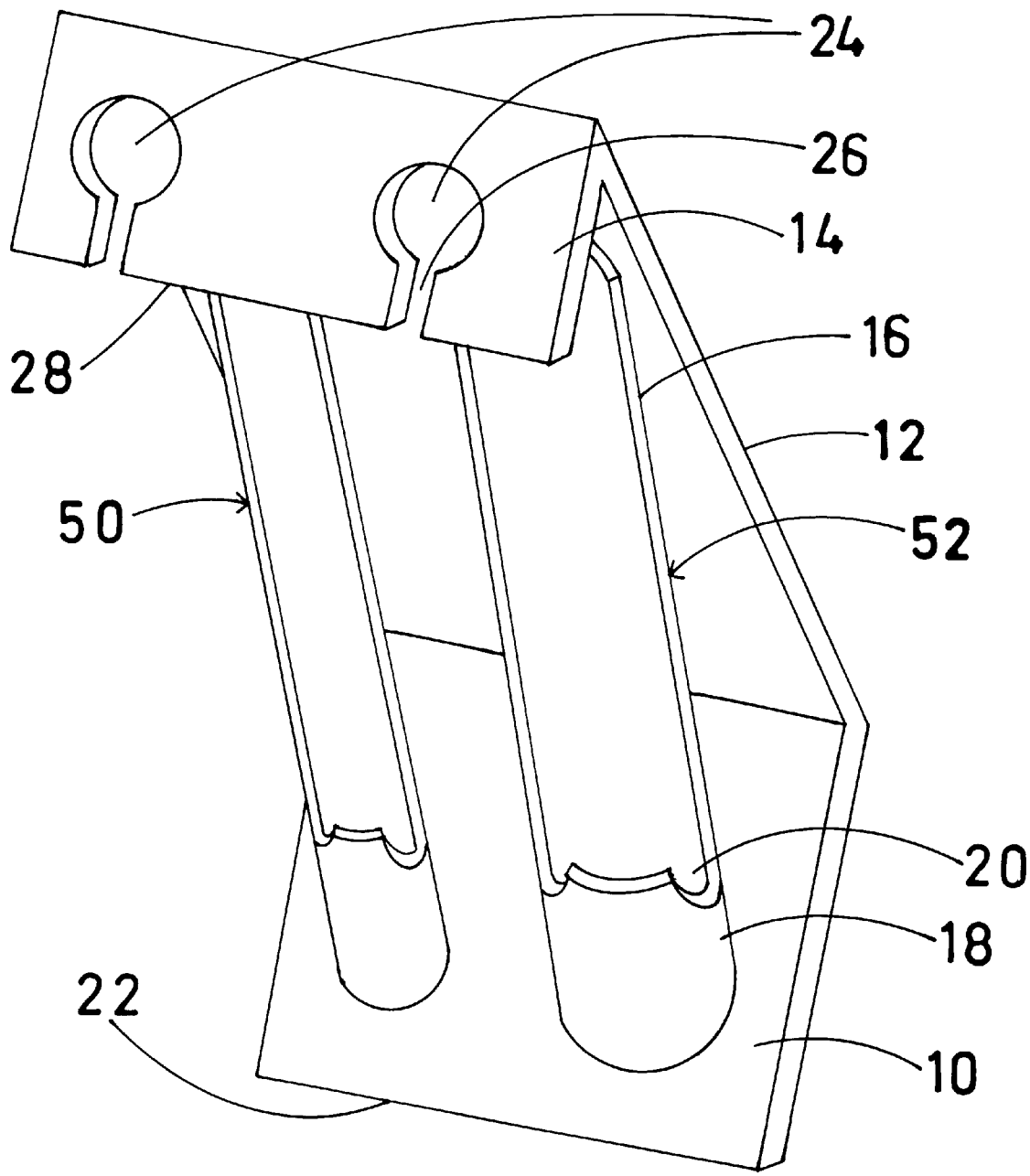
FIG. 1 shows a perspective view of Dialysis Bag Holder.

REFERENCE NUMERALS IN DRAWINGS 10 bottom plate
12 vertical plate
14 top plate
16 cradle tube
18 cup
20 notch
22 front edge of bottom plate
24 hole
26 groove
28 front edge of top plate
30 modified cradle
32 collar
34 modified "V" cradle
36 ring
38 thick wall
40 thin wall
42 short arm
44 long arm
46 support plate
48 point of contact
50 narrow cradle tube
52 broad cradle tube
54 vertical column
56 funnel
58 stem of funnel
60 dialysis bag
62 liquid sample
64 dialysis bag clamp
66 residual dialysis tube
68 twine

DETAILED DESCRIPTION OF THE INVENTION

Figure 2:
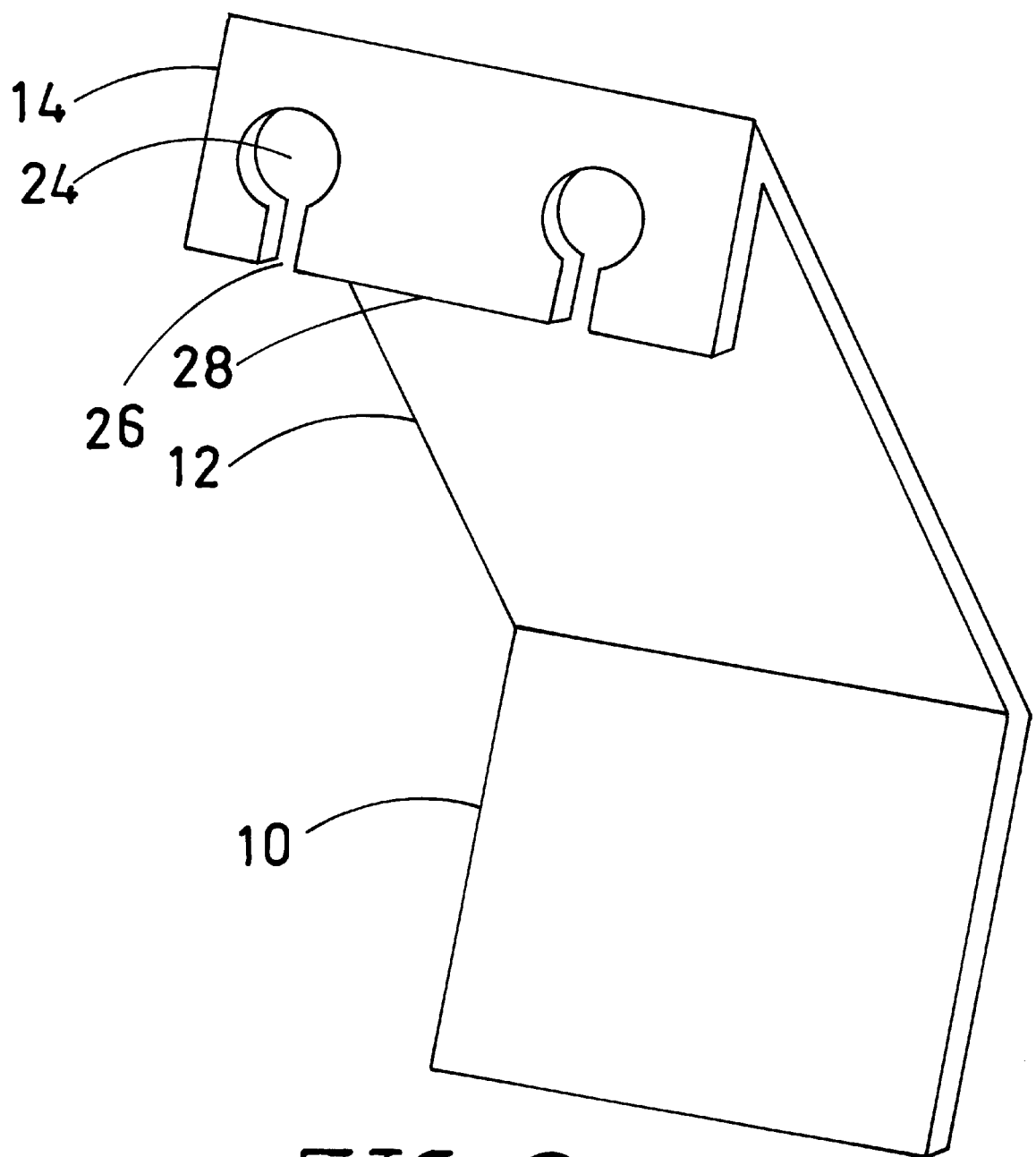
FIG. 2 is a lateral view of Dialysis Bag Holder.

A perspective view of the first preferred embodiment of Dialysis Bag Holder is shown in FIG. 1. The unit has bottom, vertical and top plates as well as cradle tubes. A uniformly thick continuous piece of acrylic plate ranging in length between 18" and 24", width between 5" and 10" and thickness between ⅖" and ⅜" is cut, shaped by machining and then bent by applying heat. The first bent is made at a distance closely between 5" to 7", having an angle between 70 and 90 degrees, to obtain a flat bottom plate 10 and a slightly longer but tilted vertical plate. A second bent, on the side of bottom plate, having an angle between 90 and 110 degrees, is made in the tilted vertical plate at a distance between 6" to 10". This gives a vertical plate 12 with a short top plate 14 at the end, running approximately parallel in the same direction as that of bottom plate. Thus all the three plates are derived from one piece of material without any need for nuts and bolts (FIG. 2). Slightly thick or thin, clear or colored acrylic sheet can also be used for this purpose. Also, three separate pieces can also be joined to obtain the described shape.

The bottom plate holds cradle tubes 50, 52 and the vertical plate. The vertical plate in turn supports the top of cradle tubes on one hand and holds the top plate on the other. The top plate has holes 24 ranging in diameter between 0.3" to 1.5", located immediately over the cradle tubes. From the broad end 28 of top plate, a groove 26 ranging approximately in width from 0.3" to 0.5" is cut to communicate with each hole. The groove gives the option of placing funnel directly into the hole or indirectly by sliding the stem of funnel through the groove (FIG. 2).

Figure 3:
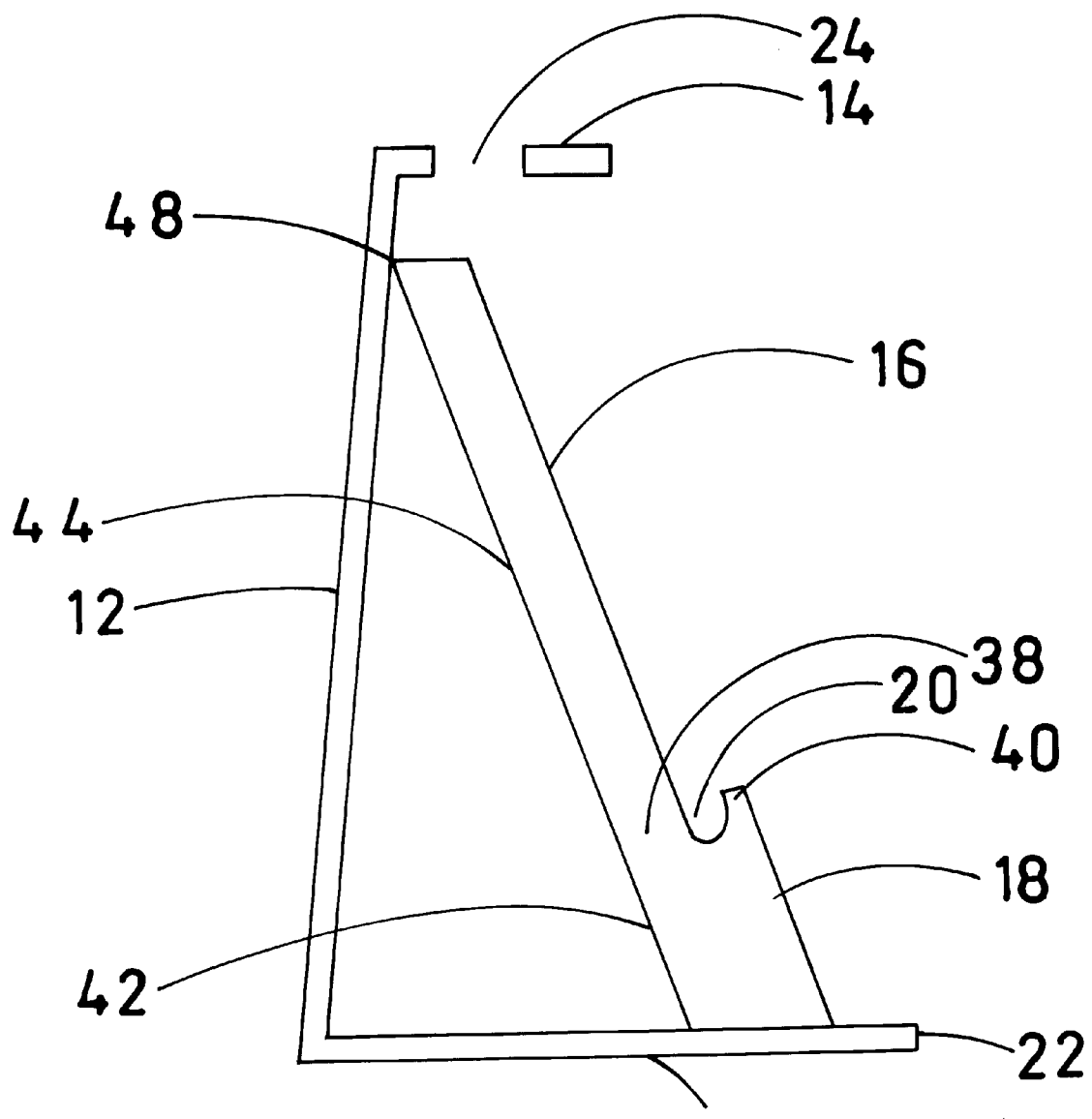
FIG. 3 shows a perspective view of bottom, vertical and top plates.

The tube for cradle ranges in length between 6" and 10", diameter between 1" and 3" and wall thickness between ¹⁄₁₆" and ⅖". From one end, leaving a 0.5" to 1.5" long tube intact, a hole ranging in diameter between 0.5" to 1" is drilled. The hole, whose center is kept slightly away from the center of the width of tube, is made to cut both sides. This results in a tube having a short arm 42 and a long arm 44 (FIG. 2) separated by a hole, which has a slightly thick wall 38 on one side and a slightly thin wall 40 on the other. From the middle of thin wall, first, a transverse cut is made towards the center of hole. From the tip of long arm, in the middle of the tube, a longitudinal cut going all the way to the hole is made. This longitudinal cut is at right angle to the first transverse cut. These cuts and the hole make the long arm open on one side with a notch 20 at the top of short arm. The open side of long arm becomes the front side. The bottom of short arm is then cut at an angle between 55 and 70 degrees making sure that when tube is attached, the open side of long arm becomes the front side having an upward inclined position. The resulting product is referred as cradle tube 16. The lower end of cradle tube is then attached close to the front edge 22 of the bottom plate leaving some gap to the sides. Approximately, a 1" space is given between adjacent cradle tubes (FIG. 1). The point of contact 48 between the vertical plate and the back of cradle tube is then attached (FIG. 3). Solvent adhesive is used to attach cradle tubes to plates.

The short arm of the tube serves as the cup 18 of cradle. The side of vertical plate 12 can be used to lift and carry the unit from place to place.

Operation

Figure 10:
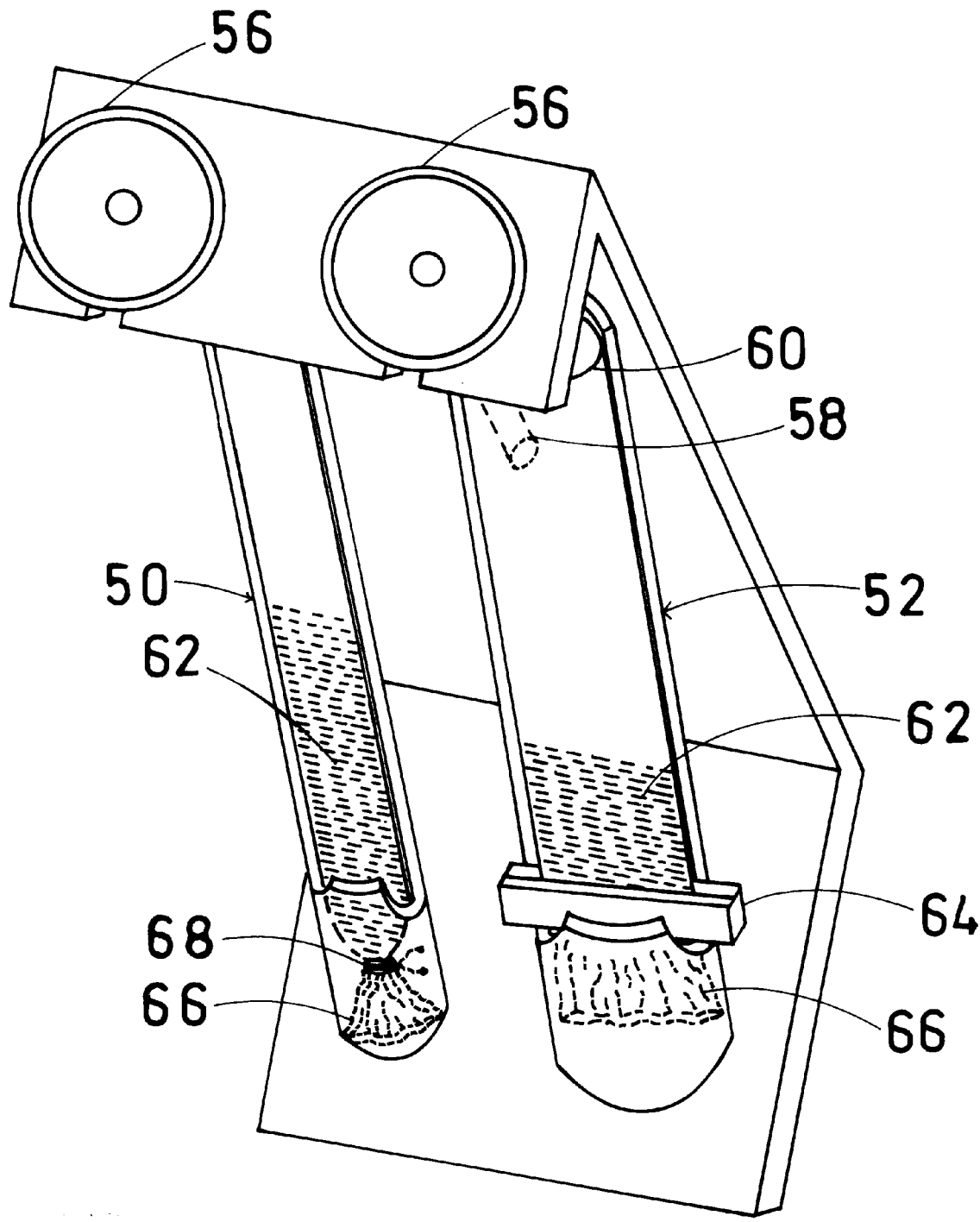
FIG. 10 shows a Dialysis Bag Holder holding dialysis bags and funnels.
Figure 11:
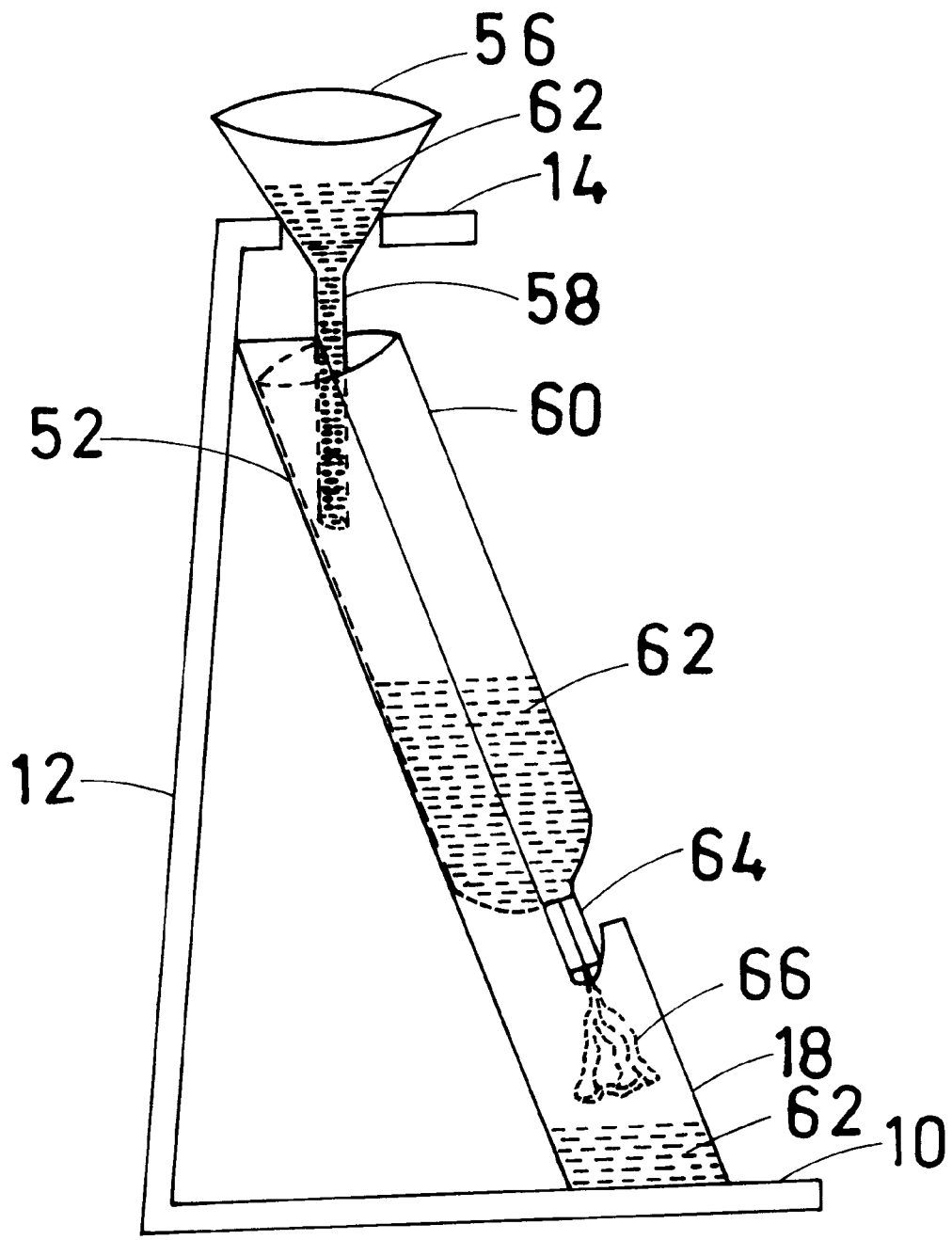
FIG. 11 shows a side view of the apparatus with a dialysis bag, a funnel and the cup with liquid saved.

To use Dialysis Bag Holder, the investigator does the following in sequence:

1. Closes one end of dialysis tube with twine 68 or clamp 64 leaving at least half inch piece 66 below, as extra.
2. Places the bag 60 in cradle. If twine is used, allows the bag to sit in the cup. If clamp is used, allows it to rest in the notch 20 located at the top of cup (FIG. 10, 11).
3. Presses the rest of bag gently so that membrane on one side makes contact with the concave surface of cradle tube.
4. Opens the mouth of bag by gently pulling only the outer membrane with forceps.
5. If sample volume is large, places a funnel 56 in the hole 24 of top plate 14 (FIG. 10, 11).
6. Introduces the stem 58 of funnel into the dialysis bag.
7. Applies a clip to keep dialysis bag stay on the funnel stem, as a safety precaution.
8. Adds sample liquid 62 leaving enough room for closing the bag.
9. If sample volume is small, uses a pipette to add sample to the bag leaving some room for closing.
10. Closes the top of bag either with twine or with clamp.
11. Takes out bag from the cradle tube and checks for leaks of sample.

12. Places the bag in buffer and dialyzes.
13. After dialysis, takes out the bag from buffer and returns to the cradle tube.
14. Cuts the bag just below the knot or opens clamp at the top.
15. Collects the sample from dialysis bag by using a pipette. If sample volume is large. carefully empties the bag in a clean beaker. Then, gently squeezes the bag to collect any trace amounts of sample present.
16. Discards the empty bag, and
17. Rinses and air dries the Dialysis Bag Holder for next use.

Other Preferred Embodiments

Figure 4:
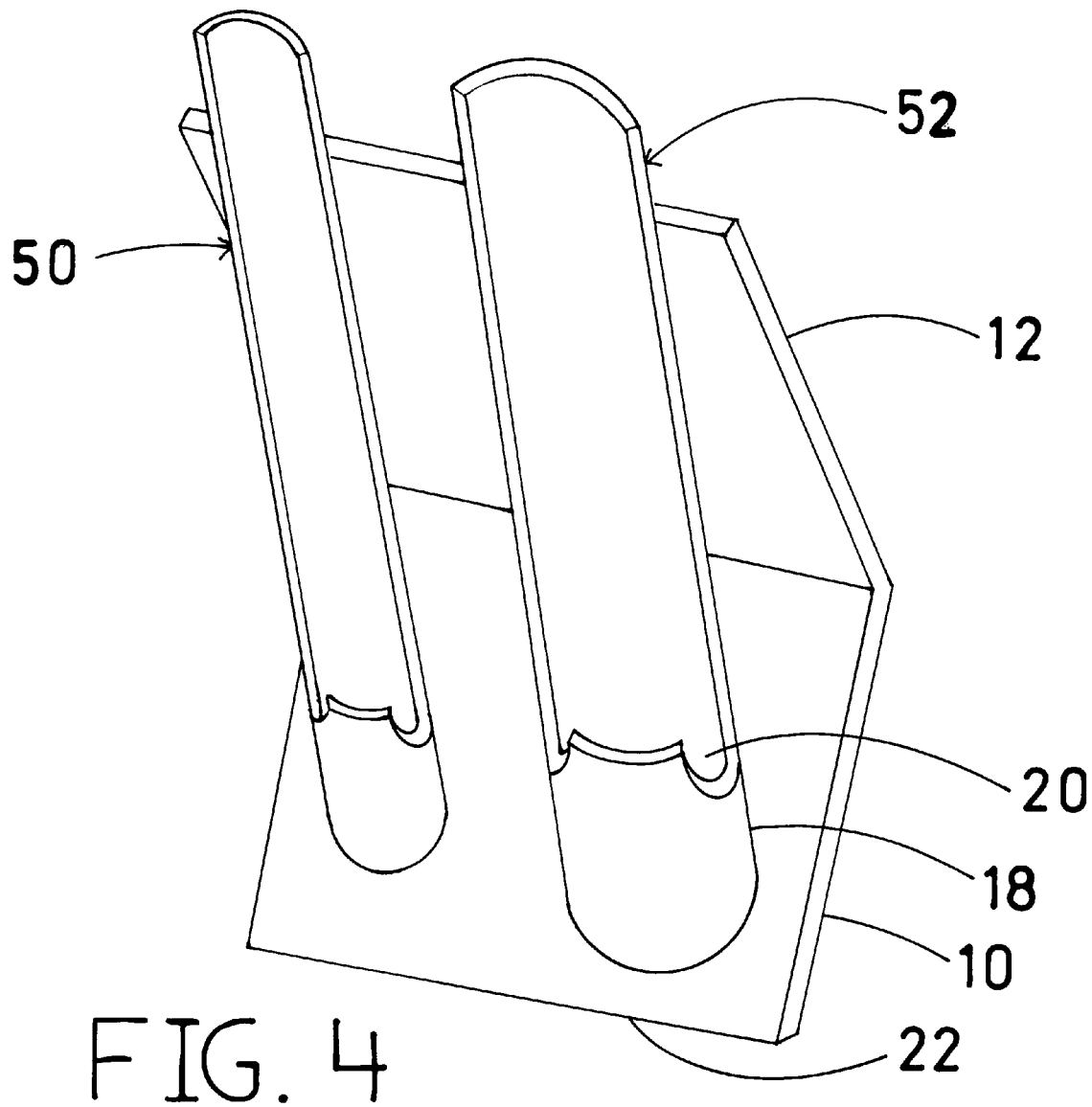
FIG. 4 is a perspective view of Dialysis Bag Holder without top plate.

The second preferred embodiment is shown in FIG. 4. It requires a plate ranging in length between 10" to 16". The plate is bent approximately in the middle of its length with an angle between 60 to 75 degrees to obtain a flat bottom plate 10 and a slanted vertical plate 12. Narrow 50 and broad 52 cradle tubes are then attached to the bottom plate, making sure that they have point of contact 48 with vertical plate to derive support at the back. The disadvantage with this embodiment is it does not have a top plate for holding funnel. However, samples of reasonable volume can be easily added to dialysis bags with a pipette.

Figure 5:
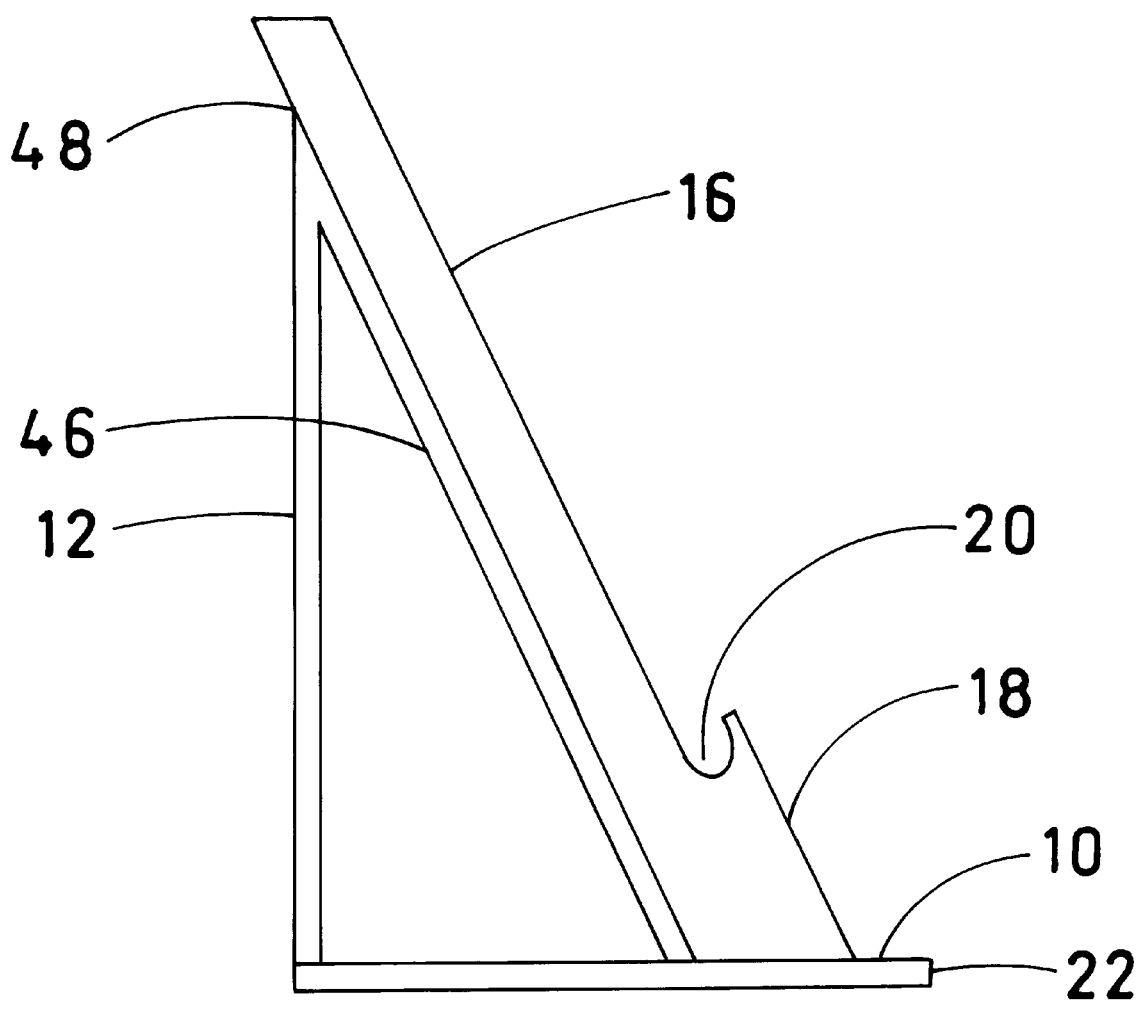
FIG. 5 is a side view of Dialysis Bag Holder containing support plate.

The third preferred embodiment is shown in FIG. 5. It requires a bottom plate 10 ranging in length between 5" to 8" and width between 5" to 8". It also requires a separate second plate ranging in length between 12" and 16". The second plate is then bent approximately in the middle of its length with an angle between 35 to 45 degrees, so that when the edge of one vertical plate 12 is attached to the bottom plate, the other support plate 46 makes an angle between 60 and 70 degrees to the bottom plate. Such a plate supports the back of cradle tube along its entire length. Several narrow 50 or broad 52 or both narrow and broad cradle tubes are attached to the bottom plate. This type of embodiment gives longer area of support to the back of cradle tubes and is useful for loading different types of samples into dialysis bags without cross-contamination. The drawback is that it does not have a top plate for holding funnel.

Figure 6:
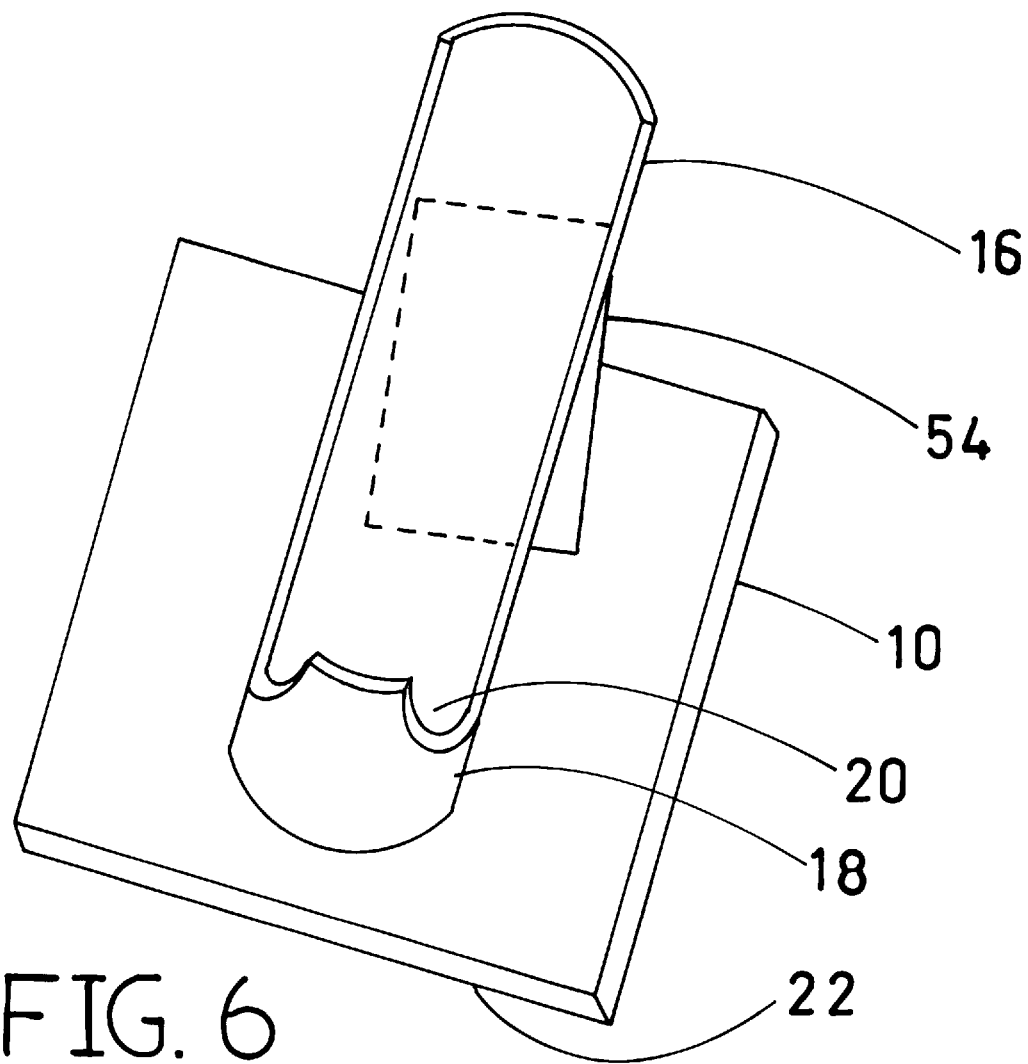
FIG. 6 shows Dialysis Bag Holder with a vertical column.

The fourth preferred embodiment is shown in FIG. 6. It is simple in construction. It contains a bottom plate 10 with attached cradle tube 16. A vertical column 54, attached to the bottom plate, supports the back of cradle tube. This type of unit is useful for handling samples of small volume. The disadvantage is that, it has no accommodation for funnel.

Figure 7:
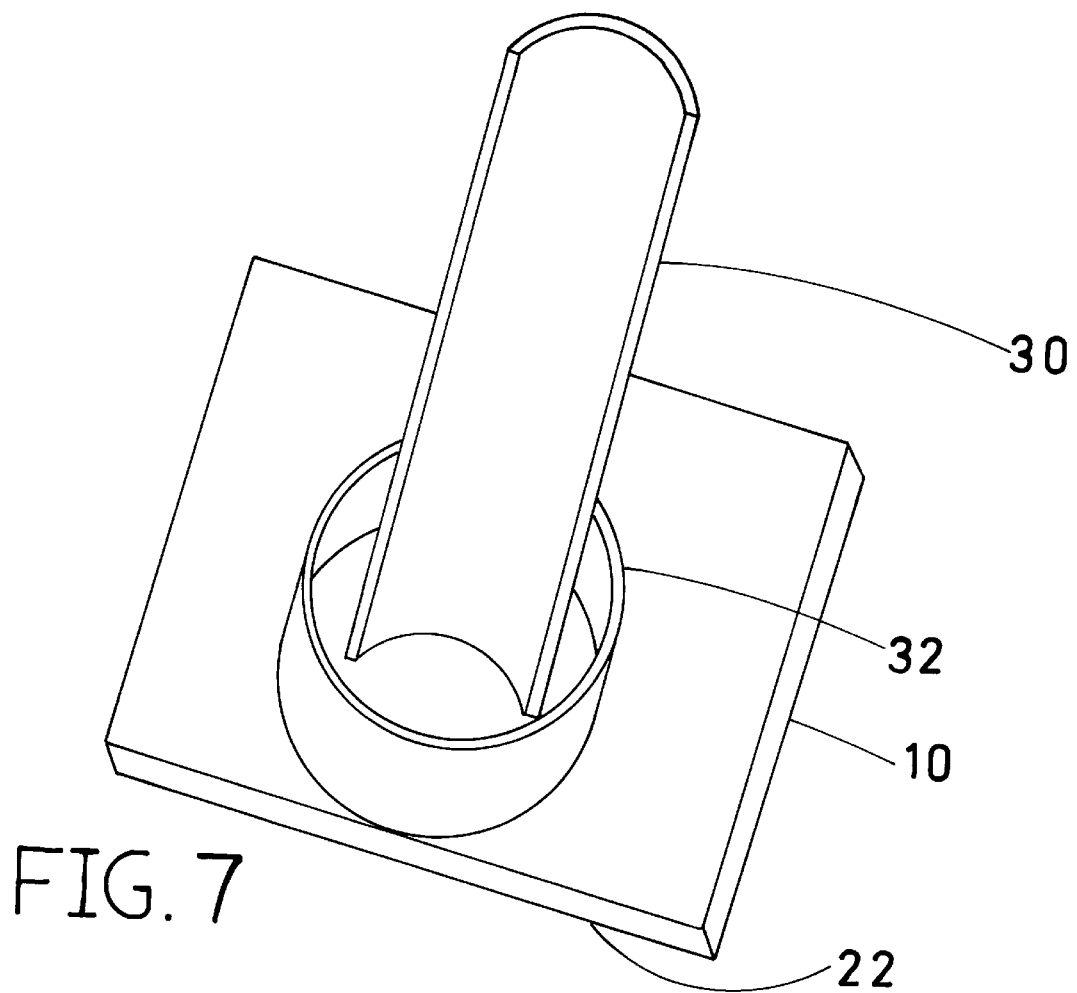
FIG. 7 is a Dialysis bag Holder with a modified cradle and a collar.

The fifth preferred embodiment, shown in FIG. 7, contains a bottom plate 10 and a cradle, derived by further modification of the cradle tube. The modified cradle 30 has no cup and no notch. A longitudinally cut open half-tube forms the modified cradle. The modified cradle is attached to the top of bottom plate at an angle. A collar 32 of suitable diameter having a height between ⅛" to 1" surrounds the base of modified cradle. The collar is fixed permanently to the bottom plate leaving some space around the base of modified cradle. The main advantage of the collar, besides restricting sliding of dialysis bag at the bottom, is that, it saves any accidentally spilled sample. All other features and their alterations described for the cradle tube can be applied to the modified cradle as well.

Figure 8:
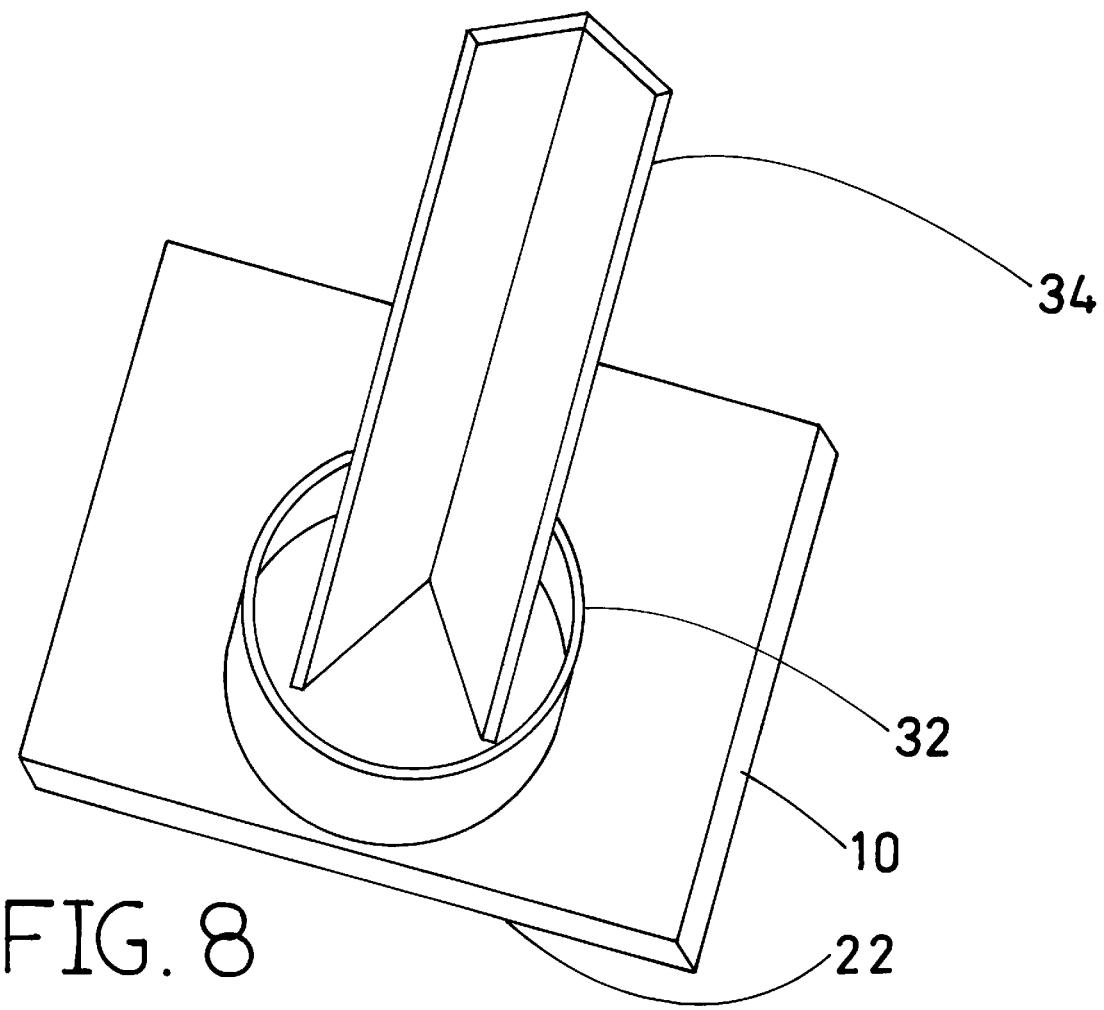
FIG. 8 is a Dialysis Bag Holder with a modified "V" shaped cradle and a collar.

The sixth preferred embodiment, FIG. 8, contains a modified cradle that looks like "V" in its cross-section. It is fabricated from two long narrow strips joined along their long margins. This type of modified "V" cradle 34 is attached to a base plate 10 at an angle and is surrounded by a collar 32 having suitable height. All other structural features and modifications described for the cradle tube can be applied to this type of cradle as well.

Figure 9:
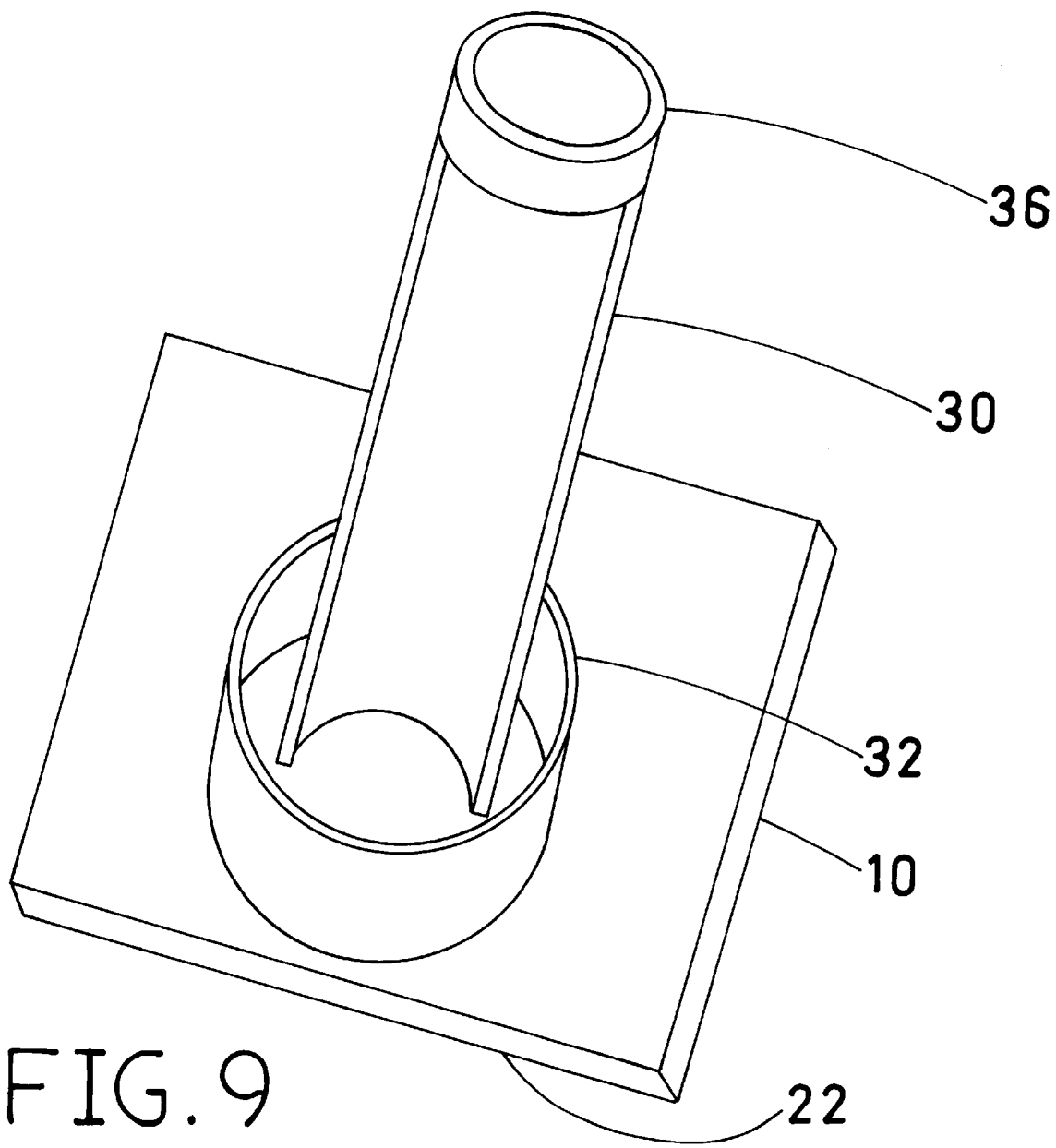
FIG. 9 is a perspective view of Dialysis Bag Holder with a modified cradle containing ring.

The seventh preferred embodiment is shown in FIG. 9. Cradle tube and its modifications contain a ring 36 at the top to hold a funnel for adding samples of reasonable volume. The disadvantage is that unit has no top plate. All other structural features and modifications described for cradle tube can be applied to this type of embodiment.

Summary, Ramifications and Scope

Accordingly, the reader can see, this invention is very useful for adding biological sample to dialysis bag, safely. The cradle tube holds the bag without letting it slide. Similarly, the cup of cradle tube surrounds the lower part of dialysis bag that is tied with twine. The notch at the top of cup restrains the movement of bag closed with a clamp. Also, the cup collects any sample spilled by accident. Therefore, the cup not only eliminates contamination of work area but also prevents loss of valuable sample. Similar purpose of the cup is obtained by collar present in other embodiments. A major advantage of different embodiments described is that each cradle tube permits loading of dialysis bags of varying lengths. After use, all the described embodiments can be rinsed, air dried and stored easily.

While the basic details of Dialysis Bag Holder are shown in various embodiments described above, it is understood that additional changes in size, shape, structure and materials can be made without greatly departing from the original conception. However, some other modifications of the invention with advantages and disadvantages are described below.

Dialysis Bag Holder contains a handle to lift and carry the unit. However, providing a handle requires additional material and work.

The unit contains several cradle tubes of same length and width. The benefit is that one can process different samples or different fractions of one sample having similar volume, without causing cross-contamination.

Bottom plate contains several cradle tubes of same length but of different diameters. The gain with this unit is that samples of different volumes can be loaded into dialysis bags of different diameters.

The unit contains cradle tubes of same diameter but of different lengths. This type of unit is useful in laboratories where both the analytical and the preparative studies are performed. With this unit, samples of small volume and also of large volume can be added to short and long dialysis bags.

Dialysis Bag Holder contains cradle tubes located on one side. The benefit is all samples can be loaded into bags on the same side.

Bottom plate contains cradle tubes located on both sides. The advantage is same unit can be used to load samples by more than one person at the same time.

Bottom plate contains squared tube converted as cradle. The setback is lack of concave surface to give good fit to the cylindrical dialysis bag. Also, squared tubes are not easily available.

Several of the above mentioned and other features can be mixed and matched to obtain other types of embodiments.

Discussion

There are many drawbacks in using intact tube to hold dialysis bag for loading biological sample. One problem is that dialysis bags of different lengths and diameters can not be loaded by using the same tube. For instance, it is hard to have open access to a short dialysis bag in a relatively long tube. Similarly, a major difficulty occurs after adding sample. The added liquid makes dialysis bag a tight fit in the tube. Any attempt to remove the bag creates vacuum from below. Excessive force to remove bag results either in a break or in a stretch of the membrane. Generally, stretching causes unacceptable changes in the controlled pore size of membrane which ultimately results in the loss of valuable sample. Therefore, in this invention, intact tubes are modified into cradles having only short cups at the bottom. These cradle tubes are modified even further not to have any cup but to have a collar of desired height surrounding the base of modified cradle, which is a longitudinally cut open tube.

The open access of cradle tube makes working with dialysis bag easy. The added solution inflates the bag making it firm and cylindrical. The concave surface and the slanted position easily roll the inflated cylindrical bag to the middle of cradle tube where it remains stable. Besides, the weight of sample by pressing the membrane of bag against the cradle tube, increases interaction between the two surfaces. The shapes of both components also offer the best fit. The two lateral sides of cradle tube prevent the bag not to roll out of its position. The cup of cradle tube or the collar surrounding the base of modified cradle also prevent slip of bag at the bottom. In brief, all the above mentioned factors promote stability of dialysis bag in the cradle tube.

The location of funnel also makes it suitable for adding solution directly to dialysis bag. The solution instantly goes to the bottom of bag, without dragging the delicate membrane down. However, as an additional precaution, a clip can be easily placed over the membrane surrounding the narrow stem of funnel due to the open access to the cradle tube. The top plate securely holds the funnel in its place, without imposing any weight on the cradle. In embodiments where top plate is eliminated, a ring attached to the top end of cradle holds the funnel.

By using Dialysis Bag Holder, collection of dialyzed sample with a pipette is easy. Surface tension between the membrane of bag and the tube, and the slanting position of the cradle keep the sac stay in its place as the level of solution decreases. As the collection progresses, to eliminate undue obstruction, the empty portion of the bag can be cut above the level of liquid, when ever needed. Therefore, this unit not only helps in adding or removing valuable biological samples from dialysis bags, but also prevents potential spills. It is very convenient, simple to use and easy to store.

I claim:

1. A Dialysis Bag Holder for restraining a delicate, collapsible membrane bag for adding solution, said Dialysis Bag Holder comprising:

a bottom plate, said bottom plate having a front end and a back end, a vertical plate extending upwardly from said back end of said bottom plate, and a top plate extending forwardly from said vertical plate, said top plate remaining parallel to said bottom plate; said bottom plate, said vertical plate and said top plate being made from a unitary continuous piece of the same material;

at least one cradle for supporting a length of said bag, said cradle having a front end and a back end, said front end of said cradle located adjacent said front end of said bottom plate, said back end of said cradle raised to a substantial height below said top plate so as to make said cradle assume a predetermined rearwardly ascending slope; and said front end of said cradle further forming at least one cup for receiving the lower end of said bag, said cup having a bottom end and an upper end, said bottom end of said cup sitting on said front end of said bottom plate.

2. The Dialysis Bag Holder of claim 1, wherein said bottom plate, said vertical plate, said top plate, and said cradle are made from acrylic.

3. The Dialysis Bag Holder of claim 1, wherein said top plate has a front end and a back end.

4. The Dialysis Bag Holder of claim 3, wherein a groove cut from said front end of said top plate has suitable length and width for sliding the stem of a funnel.

5. The Dialysis Bag Holder of claim 4, wherein said groove communicates with a hole suitably located inside said top plate so as to seat the top of a funnel slided through said groove into said hole.

6. A Dialysis Bag Holder for restraining a delicate, collapsible membrane bag for adding solution, said Dialysis Bag Holder comprising:

a bottom plate, a vertical plate and a top plate;

said bottom plate, said vertical plate and said top plate being made from a unitary continuous piece of the same material;

at least one cradle for supporting a length of said bag said cradle having a front end and a back end, said front end of said cradle located adjacent said bottom plate, said back end of said cradle placed at a substantial height below said top plate so as to make said cradle assume a predetermined rearwardly ascending slope toward said vertical plate and said top plate; and said front end of said cradle further forming at least one cup for receiving the lower end of said bag, said cup having a bottom end and an upper end, said bottom end of said cup sitting on said bottom plate.

7. The Dialysis Bag Holder of claim 6, wherein said cradle has a concave upper surface along its length above said cup.

8. The Dialysis Bag Holder of claim 7, wherein said concave upper surface of said cradle faces away from said vertical plate for providing open access so that said bag can be placed with ease in said concave upper surface of said cradle.

9. The Dialysis Bag Holder of claim 8, wherein said concave upper surface has lateral elevated edges along its length, on both sides of said concave upper surface so as to prevent rollover of said bag when in said concave upper surface of said cradle.

10. The Dialysis Bag Holder of claim 6, wherein said cradle is attached by said cup at an acute angle to said bottom plate, so as to give said cradle said predetermined rearwardly ascending slope.

11. A Dialysis Bag Holder for restraining a delicate, collapsible membrane bag for adding solution, said Dialysis Bag Holder comprising:

a bottom plate, a vertical plate and a top plate; said bottom plate, said vertical plate and said top plate being made from a unitary continuous piece of the same material;

at least one cradle for supporting a length of said bag, said cradle having a front end and a back end, said front end of said cradle located adjacent said bottom plate, said back end of said cradle placed at a substantial height below said top plate so as to make said cradle assume a predetermined rearwardly ascending slope toward said vertical plate and said top plate; and said front end of said cradle further forming at least one cup, said cup formed of a generally cylindrical wall having upper and lower edges, said bottom end of said cup sitting on said bottom plate.

12. The Dialysis Bag Holder of claim 11, wherein said bottom end of said cup is permanently attached to said bottom plate along the lower edge of said vertical wall.

13. The Dialysis Bag Holder of claim 11, wherein said upper end of said cup has at least two notches, in opposing position, on said wall of said cup for securing a dialysis bag clamp.

14. The Dialysis Bag Holder of claim 11, wherein the interior of said cup communicates with a concave upper surface of said cradle so as to make any accidentally spilled liquid from a dialysis bag present in said concave upper surface of said cradle flow into said cup for recovery.

* * * * *